US00PP16647P2

(12) United States Plant Patent
Schmulling

(10) Patent No.: US PP16,647 P2
(45) Date of Patent: Jun. 13, 2006

(54) ***OSTEOSPERMUM* PLANT NAMED 'BALSERWIBLI'**

(50) Latin Name: *Osteospermum hybrida*
Varietal Denomination: Balserwibli

(75) Inventor: Markus Schmulling, Billerbeck (DE)

(73) Assignee: FA. Wilhelm Schmulling, Billerbeck (DE)

( * ) Notice: Subject to any disclaimer, the term of this patent is extended or adjusted under 35 U.S.C. 154(b) by 87 days.

(21) Appl. No.: 11/022,604

(22) Filed: Dec. 27, 2004

(51) Int. Cl.
*A01H 5/00* (2006.01)

(52) U.S. Cl. ..... Plt./360

(58) Field of Classification Search ..... Plt./360
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Osteospermum* plant named 'Balserwibli' characterized by its single inflorescence form with "spoon" shaped, white-colored ray florets with "eye" and blue-colored disc florets, medium green-colored foliage, freely branching character, and compact and upright growth habit.

1 Drawing Sheet

Latin name of the genus and species of plant claimed: *Osteospermum hybrida.*
Variety denomination: 'Balserwibli'.

BACKGROUND OF THE INVENTION

The present invention relates to a new and distinct cultivar of *Osteospermum* plant botanically known as *Osteospermum hybrida* and hereinafter referred to by the cultivar name 'Balserwibli'.

The new *Osteospermum* originated in a controlled breeding program in Billerbeck, Germany, during August 1999. The objective of the breeding program was the development of *Osteospermum* cultivars that are freely branching, have a compact and upright growth habit, are freely flowering, and have unique flower coloration.

The female parent of the new cultivar was the proprietary *Osteospermum hybrida* breeding selection designated 09-19-98, not patented, characterized by its white-colored ray florets, yellow-colored disc florets, and vigorous growth habit. The male parent of the new cultivar was the proprietary *Osteospermum hybrida* breeding selection designated 35-3-99, characterized by its small leaves and compact habit. Seed from the above stated cross-pollination was germinated and grown to maturity. One plant from within the progeny was discovered and selected by the inventor during April 2000 in a controlled environment at Billerbeck, Germany.

Asexual reproduction of the new cultivar by terminal stem cuttings since April 2000 at West Chicago, Ill. has demonstrated that the new cultivar reproduces true to type, with all the characteristics as herein described, firmly fixed and retained through successive generations of such asexual propagation.

SUMMARY OF THE INVENTION

The following characteristics of the new cultivar have been repeatedly observed and can be used to distinguish 'Balserwibli' as a new and distinct cultivar of *Osteospermum* plant:

1. Single inflorescence form with "spoon" shaped, white-colored ray florets with "eye" and blue-colored disc florets.
2. Medium green-colored foliage.
3. Freely branching character.
4. Compact and upright growth habit.

Plants of the new cultivar differ from plants of the female parent primarily in flower color and growth habit and from plants of the male parent primarily in leaf size.

Plants of the new cultivar are most similar to the cultivar Brightside, U.S. Plant Pat. No. 10,596. However, in side-by-side comparisons, plants of the new cultivar differ from plants of 'Brightside' in the following characteristics:

1. Plants of the new cultivar are taller than plants of 'Brightside'.
2. Plants of the new cultivar have larger inflorescences than plants of 'Brightside'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describe the colors of the new cultivar. The plants were grown in 10 cm pots for 17 weeks in a greenhouse at West Chicago, Ill.

DETAILED BOTANICAL DESCRIPTION

Figure 1:
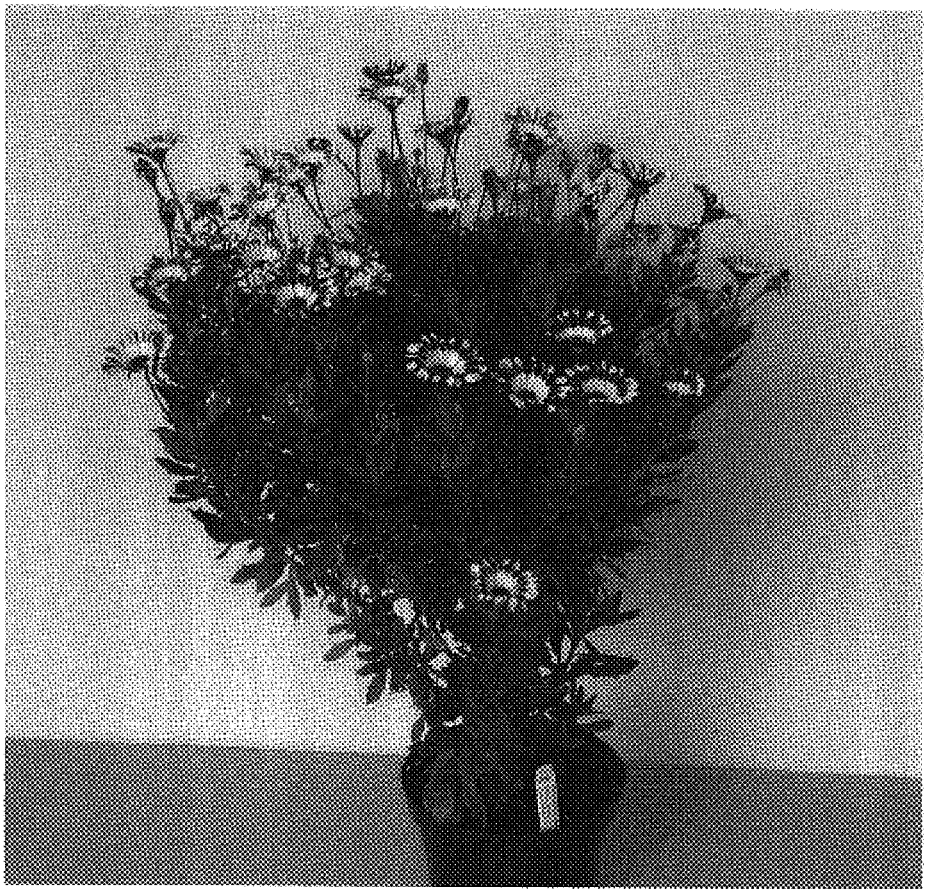
FIG. 1 illustrates a side view of the overall growth and flowering habit of the new cultivar with one plant per pot.
Figure 2:
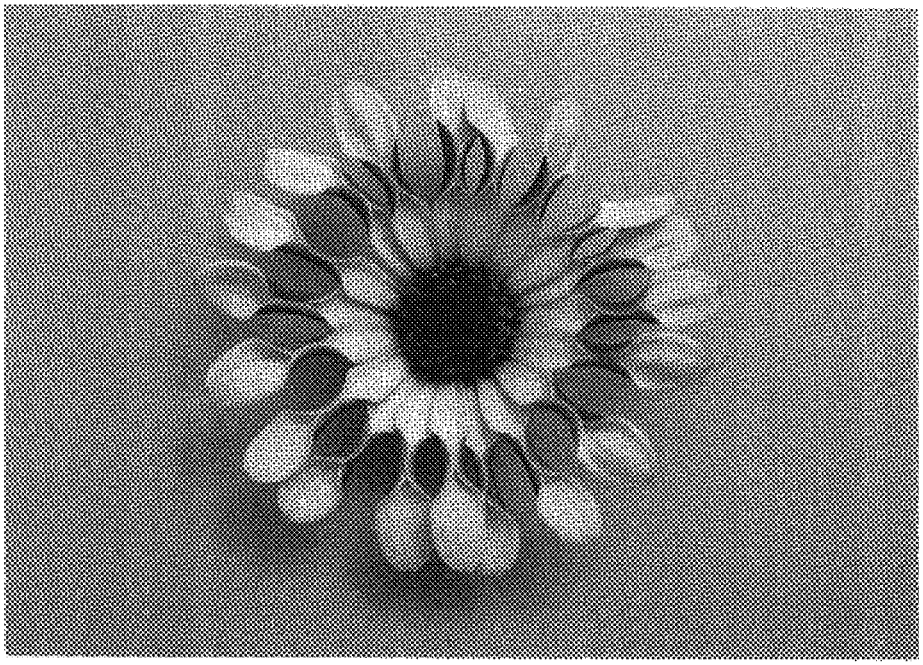
FIG. 2 illustrates a close-up view of an individual flower of the new cultivar.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Sep. 27, 2004 between 1:00 and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 17 weeks while utilizing a soilless growth medium. Greenhouse temperatures were maintained at approximately 60°–75° F. (15°–24° C.) during the day and approximately 45°–55° F. (7°–13° C.) during the night. Greenhouse light levels were maintained at 5,000 to 9,000 footcandles during the day.

Botanical classification: *Osteospermum hybrida* cultivar Balserwibli.

Parentage:

*Male parent.*—Proprietary breeding selection 35-3-99, not patented.

*Female parent.*—Proprietary breeding selection 09-19-98, not patented.

Propagation:

*Type cutting.*—Terminal stem.

*Time to initiate roots.*—Approximately 9 to 12 days.

*Time to produce a rooted cutting.*—Approximately 21 to 28 days.

*Root description.*—Fine, fibrous.

*Rooting habit.*—Freely branching.

Plant description:

*Crop time.*—Approximately 10–13 weeks from a rooted cutting in a 10 cm pot.

*Growth habit.*—Compact, freely branching.

*Form.*—Upright.

*Size.*—Height: Approximately 31.8 cm from soil level to top of plant plane. Width (area of spread): Approximately 26 cm.

*Branch.*—Quantity per plant: Approximately 3. Strength: Strong. Length from soil level to base of peduncle: Approximately 12.9 cm. Diameter: Approximately 5.3 mm. Internode length at middle of branch: Approximately 1.6 cm. Texture: Glabrous. Color: 144A.

*Foliage.*—Quantity per branch: Approximately 16. Type: Simple. Fragrance: Strong, resinous. Arrangement: Alternate. Aspect: At an acute angle to the stem. Shape: Elliptic, Pinnatified. Apex: Acute. Base: Decurrent. Margin: Broadly dentate. Venation pattern: Pinnate. Length: Approximately 5.9 cm. Width: Approximately 2.6 cm. Texture of upper and lower surfaces: Pubescent. Color of upper surface of mature foliage: Slightly more yellow than 137A with venation of 145A. Color of lower surface of mature foliage: 137C with venation of 144A.

Flowering description:

*Time to first flower.*—Approximately 10–13 weeks from planting of rooted cutting.

*Flowering habit.*—Freely flowering under outdoor growing conditions with substantially continuous blooming from spring through autumn and year round in greenhouse environment.

*Flower arrangement.*—Solitary, terminal.

Inflorescence description:

*Appearance/type.*—Composite, persistent. Shape: Round. Aspect: Facing upward or outward. Disc and ray florets develop acropetally on a capitulum. Fragrance: None.

*Quantity of flowers and buds per plant.*—Approximately 2 inflorescences and 10 buds.

*Size.*—Diameter: Approximately 4.9 cm. Depth: Approximately 2.1 cm.

*Lastingness of inflorescence.*—Approximately 6–8 days.

*Bud.*—Rate of opening: Generally takes from 3–5 days for buds to progress from first color to fully open flowers. Shape: Elliptic. Diameter: Approximately 1 cm. Depth: Approximately 1.5 cm. Color: 150A.

*Ray florets.*—Quantity per inflorescence: Approximately 21, arranged in a single whorl. Arrangement: Very slightly overlapping. Aspect: Slightly concave. Shape: Ligulate. Apex: Emarginate with three tips. Base: Attenuate. Margin: Entire, constricted in center forming a tube with apex being "spoon" shaped. Length: Approximately 2.7 cm. Width: Approximately 7.2 mm. Texture: Glabrous. Color of upper and lower surfaces of young and mature ray florets: Lighter than N155B.

*Disc.*—Diameter: Approximately 1 cm. Depth: Approximately 5.6 mm. Receptical diameter: 3 mm. Receptical depth: 2 mm. Receptical color: 145B.

*Disc florets.*—Quantity per inflorescence: Approximately 79. Shape: Tubular with five lobes each having an acute apex. Margin: Entire. Length: Approximately 7.8 mm. Diameter at apex: Approximately 1.9 mm. Diameter at base: Approximately 0.8 mm. Texture: Glabrous. Color of immature floret: Closest to 96A. Color of mature floret: Closest to 86B.

*Phyllaries.*—Quantity per inflorescence: Approximately 19. Arrangement: Imbricate, arranged in several rows. Shape: Lanceolate. Apex: Acuminate. Base: Truncate. Margin: Entire. Length: Approximately 1.1 cm. Width: Approximately 2.3 mm. Texture: Glabrous, papery along edges. Color of upper surface: 143A. Color of lower surface: 143B.

*Peduncle.*—Strength: Strong, pliable. Aspect: Erect. Length: Approximately 8.1 cm. Diameter: Approximately 1 mm. Texture: Sparse barbs. Color: 144A.

*Reproductive organs.*—Androecium: Present on disc florets only. Stamen quantity: 4. Anther shape: Linear. Anther length: 2 mm. Anther color: 93A. Amount of pollen: Abundant. Pollen color: 23A. Gynoecium: Present on ray and disc florets. There is one pistil per floret. Pistil length: 7 mm. Stigma shape: Globular. Stigma length: 0.5 mm. Stigma color: N92A. Style length: 4 mm. Style color: N155B. Ovary diameter: 2.5 mm. Ovary color: 145C.

Seed and fruit production: Neither seed nor fruit production has been observed.

Disease and pest resistance: Resistance to pathogens and pests common to *Osteospermum* has not been observed.

What is claimed is:

1. A new and distinct cultivar of *Osteospermum* plant named 'Balserwibli', substantially as herein shown and described.

* * * * *